United States Patent [19]

Harman, III et al.

[11] Patent Number: 4,485,001
[45] Date of Patent: Nov. 27, 1984

[54] STERILIZABLE PH ELECTRODE AND METHOD FOR PRODUCING THE SAME

[75] Inventors: John N. Harman, III, Placentia; Radhakrishna M. Neti, Brea, both of Calif.

[73] Assignee: Beckman Instruments, Inc., Fullerton, Calif.

[21] Appl. No.: 582,111

[22] Filed: Feb. 21, 1984

[51] Int. Cl.$^3$ ............................................. G01N 27/36
[52] U.S. Cl. ................................... 204/408; 204/420; 204/433
[58] Field of Search ............... 204/420, 433, 1 H, 408; 324/438

[56] References Cited

U.S. PATENT DOCUMENTS

| | | | |
|---|---|---|---|
| 3,444,067 | 5/1969 | Watanabe et al. | 204/420 X |
| 3,855,098 | 12/1974 | Fletcher | 204/420 |
| 4,328,082 | 5/1982 | Neti et al. | 204/420 |

FOREIGN PATENT DOCUMENTS

| | | | |
|---|---|---|---|
| 492936 | 9/1938 | United Kingdom | 204/420 |
| 495303 | 11/1938 | United Kingdom | 204/420 |

Primary Examiner—G. L. Kaplan
Attorney, Agent, or Firm—W. H. May; P. R. Harder; E. C. Jason

[57] ABSTRACT

A pH electrode which is capable of withstanding repeated exposures to sterilizing temperatures. An electrode body having a pH sensing member is at least partially filled with a bed of electrochemically inert particles. After an internal reference is inserted into the particle bed, the bed is injected with a quantity of electrolyte which is sufficient to establish continuity between the sensing member and the internal reference, but which is not sufficient to produce destructive internal pressures when the electrode is subjected to sterilizing temperatures. The electrode is completed by forming a seal between the electrode body and the internal reference.

29 Claims, 2 Drawing Figures

U.S. Patent  Nov. 27, 1984  4,485,001
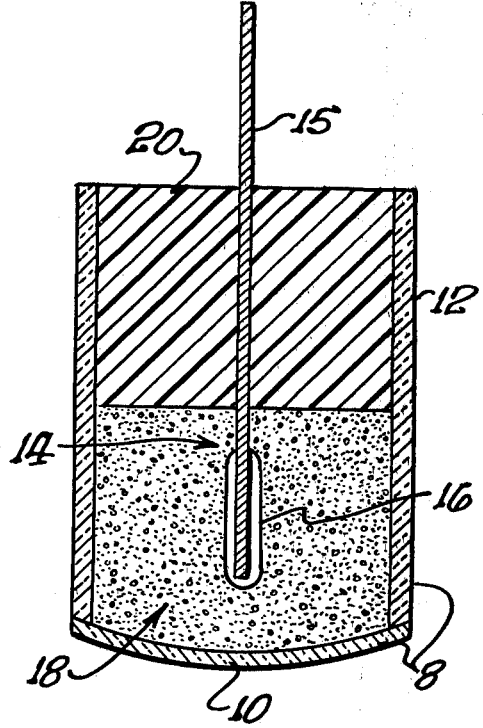
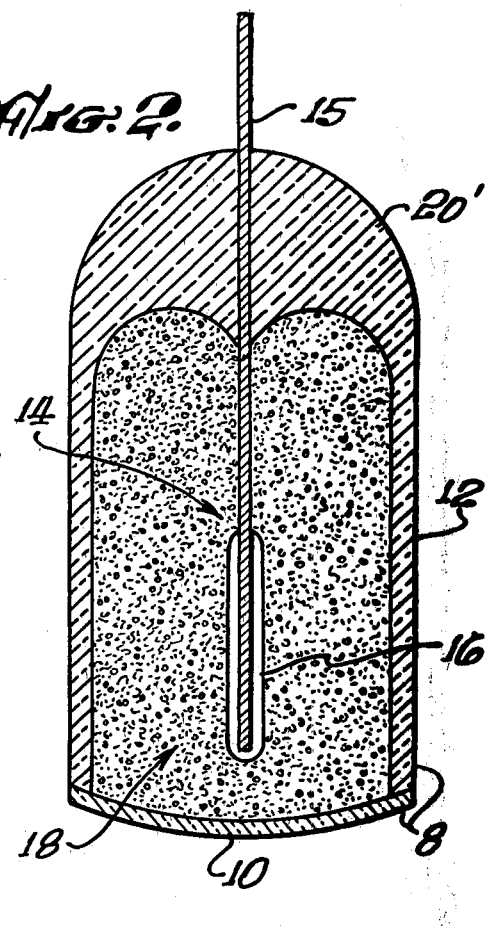

STERILIZABLE PH ELECTRODE AND METHOD FOR PRODUCING THE SAME

BACKGROUND OF THE INVENTION

The present invention relates to pH electrodes, and is directed more particularly to pH electrodes which can withstand exposure to sterilizing temperatures and to a method for producing such electrodes.

Glass pH electrodes have long been known and used to measure the hydrogen ion activity of test solutions, particularly aqueous test solutions. Such electrodes typically include an electrode body which comprises a glass pH sensitive member that is attached to one end of an electrochemically inert support member, such as a tubular piece of glass or plastic. The interior of this electrode body is typically filled with a suitable electrolyte solution, such as a dilute buffered solution of aqueous potassium chloride. This electrolyte solution serves as an electrolytic bridge between the inner surface of the glass member and an internal reference such as a silver wire that is coated with silver chloride. In use, the potential difference across the glass member tends to vary, in accordance with the well known Nernst equation, at a rate of 59 milivolts per pH unit.

pH electrodes of the above described type operate satisfactorily so long as their temperatures remain between the freezing and boiling points of their electrolytes. At temperatures below the freezing point, pH electrodes tend to become damaged by the thermal expansion that is associated with the freezing of the water in their electrolytes. Similarly, at temperatures above the boiling point, pH electrodes tend to become damaged by the internal pressure that is associated with the vaporization of the water in their electrolytes. Thus, the use of aqueous electrolyte solutions limits the range of temperatures over which glass pH electrodes can be used.

While the above described temperature limitations are acceptable in many applications, they are not acceptable in applications in which an electrode is used to measure the pH of a liquid food product or the contents of a fermentation vat. This is because applications of the latter type require the maintenance of totally or selectively sterile conditions. The latter conditions, in turn, require that all of the equipment that comes into contact with the liquid, to be measured must first be sterilized. Usually, such sterilization requires the exposure of the equipment to temperatures of approximately 140° C. for periods of several minutes. Moreover, such sterilizations must be repeated on a regular basis.

One solution to the sterilization problem has been to sterilize pH electrodes by nonthermal means, such as by exposure to ethylene oxide or other fluids having bactericidal properties. Sterilization procedures of this type, however, are undesirable because they require the removal and reinstallation of the electrode. This removal and reinstallation, in turn, is undesirable because it breaks the integrity of the liquid containment system, and thereby creates a risk that live bacteria will be introduced.

Another approach to the sterilization problem has been to use pH electrodes which have dry, solid-state electrolyte systems. Because such electrodes do not contain any liquid, they do not produce the internal pressures which damage the delicate glass pH sensing member. They also, however, show a reduced pH sensitivity and tend to produce unstable pH readings.

SUMMARY OF THE INVENTION

In accordance with the present invention, there is provided an improved pH electrode which has an aqueous electrolyte solution, but which can withstand repeated exposures to sterilizing temperatures. The present invention also includes an improved method for making such an electrode.

Generally speaking, the present invention contemplates a pH electrode in which a glass pH sensing member is coupled to an internal reference by a novel electrolytic bridge which does not produce destructive internal pressures even when the electrode is subjected to sterilizing temperatures for extended periods of time. In the preferred embodiment, this electrolytic bridge includes a bed of electrochemically inert particles which are packed to form a self-adherent but porous solid body of material. The interstices of this particle bed are occupied by a quantity of electrolyte solution which is large enough to establish electrical continuity between the sensing member and the internal reference, but which is small enough to prevent destructive internal pressures from arising within the electrode when the electrode is exposed to sterilizing temperatures. As a result, the electrode is able to provide the sensitivity and stability that is associated with electrodes which have liquid electrolytes, and yet is able to withstand repeated exposures to sterilizing temperatures.

In developing the electrode of the present invention, it has been discovered that the quantity of electrolyte which meets the above described requirements is surprisingly small, and has a relatively narrow range of values. If, for example, the quantity of electrolyte is appreciably greater than approximately 100 microliters per cubic centimeter of particle bed, the probability that the exposure of the electrode to sterilizing temperatures will result in destructive internal pressures increases rapidly. If, on the other hand, the quantity of electrolyte is appreciably less than 20 microliters per cubic centimeter of particle bed, the probability that the electrode will exhibit the desired sensitivity and stability of response will decrease rapidly. Thus, the electrode of the invention contemplates a relatively narrow range of electrolyte volume per unit volume of particle bed.

In developing the electrode of the present invention, it has also been discovered that the size of the particles in the particle bed can have a significant affect on the response of the electrode. If, for example, the maximum particle size is appreciably greater than that corresponding to approximately 100 mesh, the distribution of the electrolyte among the particles tends to become non-uniform, thereby causing the response of the electrode to vary with its orientation. If on the other hand, the maximum particle size is less than that corresponding to approximately 100 mesh, the distribution of the electrolyte tends to become relatively uniform, thereby causing the response of the electrode to be substantially independent of its orientation. This unexpected result apparently occurs because the small size of the packed particles gives rise to capillary forces which cause the electrolyte to distribute itself as a thin film which bridges the gaps between the particles and thereby affords electrical and fluidic continuity between the internal reference and the pH sensing member. Thus, both a particular range of particle sizes and a particular range of electrolyte volumes are responsible for the desirable properties of the pH electrode of the present invention.

Other objects and advantages of the present invention will be apparent from the following description and drawings in which:

DESCRIPTION OF THE DRAWINGS

FIG. 1 is a cross-sectional view of one embodiment of a pH electrode which has been constructed in accordance with the present invention, and FIG. 2 is a cross-sectional view of an alternative embodiment of the present invention.

DESCRIPTION OF THE PREFERRED EMBODIMENTS

Referring to FIG. 1, there is is shown a cross-sectional view of the preferred embodiment of the pH electrode of the present invention. This electrode has an electrode body 8 which includes a pH sensing member 10, that is composed of a suitable pH sensitive glass, and a support member 12 that is composed of glass, plastic, or other electrochemically inert material. pH sensing member 10 and support member 12 preferably comprise separate elements which are sealably attached by welding or other known processes. Members 10 and 12 need not, however, comprise separate elements. All of electrode body 8 may, for example, be composed of pH sensitive glass, provided that the thickness of one part thereof (such as region 10) has a thickness which is appreciably less than that of the remainder thereof (such as side region 12). Alternatively, regions 10 and 12 of body 8 may both be composed of non-pH sensitive glass, provided that pH sensing properties are induced in a part thereof (such as end region 10) by ion inplantation or other known processes.

The electrode of FIG. 1 also includes an internal reference 14 which here takes the form of a centrally located silver wire 15, one end of which is provided with a silver chloride coating 16. Other types of internal references, such as those which are composed of calomel may also be used if desired. Because the purpose and operation of internal references are well known to those skilled in the art, they will not be described in detail herein.

In accordance with an important feature of the present invention, electrical continuity is established between the inner surface of sensing member 10 and internal reference 14 by a bed 18 of electrochemically inert particles which has been moistened with a very small quantity of a suitable electrolyte solution, such as an aqueous solution of potassium choloride. In the preferred embodiment, the particles of bed 18 are composed primarily of silica, i.e., silicon dioxide, and, more particularly, of hydrated silica. This composition for the particles of bed 18 is preferred because the physical properties of silica are similar to those of glass sensing and support members 10 and 12. As a result, when the electrode is subjected to large changes in temperature, electrode body 8 and bed 18 will expand and contract at substantially the same rate, thereby avoiding the thermal stresses which would otherwise cause cracks in electrode body 8. This thermal tracking is also desirable because it prevents bed 18 as a whole from pulling away from sensing member 10 and thereby creating an electrical discontinuity between member 10 and internal reference 14.

In the preferred embodiment, bed 18 is preferably compressed so as to form a substantially solid mass of mutually adherent particles. The solidity of this mass not only imparts strength to the electrode, but also improves the ability of bed 18 to thermally track the expansion and contraction of electrode body 8. Forming bed 18 from a material that has a composition that is similar to that of member 10 enhances this effect by helping to assure that the particles thereof are as adherent to member 10 as they are to each other, thereby minimizing the tendency of discontinuities to form between the bed and sensing member.

While the particles of bed 18 are preferably composed of silica-based materials, these particles may, in general, be composed of any material which is electrochemically inert. The latter phrase means that the material does not react chemically with any of the other electrode materials to which it is exposed and does not otherwise affect the potential between the inner surface of member 10 and internal reference 14. Examples of materials that are sufficiently electrochemically inert to be used for the particles of bed 18 include plastics such as polyethylene and polypropylene and simple compounds such as titanium dioxide and silver chloride. Because of the high temperature coefficients of plastics, however, their use is advisable only if support member 12 is also composed of plastic.

In accordance with another important feature of the invention, the particles of bed 18 are relatively small and have a maximum size that corresponds to approximately 100 mesh, although particles having a maximum size that corresponds to approximately 250 to 300 mesh are preferred. This small particle size is desirable because it promotes the uniform distribution of the electrolyte throughout the interior of bed 18. This uniform distribution apparently occurs because the small size of the particles produces capillary forces which pull the electrolyte into the spaces between the particles and form a surface film that establishes electrical continuity between the pH sensing member 10 and internal reference 14. With larger particle sizes, the force of gravity tends to overcome capillary forces and cause the electrolyte to "pool" or collect at the lowermost point of the electrode. Such pools of electrolyte are undesirable because they cause the response of the electrode to change with changes in the orientation or temperature of the electrode. Thus, the size of the particles of bed 18 has an important affect on the operating characteristics of the electrode.

In accordance with still another important feature of the invention, the quantity of electrolyte which is present in particle bed 18 is kept at a relatively small value, such as a value in the range of 20 to 100 microliters per cubic centimeter of bed. Experiments indicate that this surprisingly small quantity of electrolyte is sufficient to establish electrical continuity between sensing member 10 and internal reference 14. Experiments also indicate that this small quantity of electrolyte is not sufficient to create destructive pressures within an electrode of conventional construction when the latter is subjected to sterilizing temperatures. Naturally, if the electrode has walls which are thicker than normal, and seals which are stronger than normal, the quantity of electrolyte that is used may be made higher than 20 to 100 microliters per cubic centimeter without depriving the electrode of the ability to withstand repeated exposures to sterilizing temperatures.

In no event, however, should the quantity of electrolyte be so large that the electrolyte occupies all of the space between the particles. Allowing the electrolyte to occupy all of the space between the particles leaves the electrode unprotected against the pressures incident to the thermal expansion of the liquid as the temperature of the electrode is raised. In addition, the quantity of electrolyte must not be so large that the electrolyte becomes mobile. This is because mobility in the electrolyte can cause the response of the electrode to vary with its orientation. All such problems are eliminated by using the miniscule quantities of electrolyte which are contemplated by the present invention.

As explained earlier, electrodes of the type contemplated by the present invention are preferably constructed in such a way that the particle bed forms a substantially solid adherent mass which contains a small substantially uniformly distributed body of electrolyte. The preferred method for constructing the electrode so as to meet these requirements includes the following steps:

1. Forming the pH electrode body. This may be accomplished, for example, by welding a suitable pH sensing member 10 such as a glass disc to a suitable support member such as a glass tube.
2. Filling at least the portion of the electrode body that is adjacent to the pH sensing member with a loosely packed mass of suitable particles.
3. Pushing the internal reference into the loosely packed mass of particles.
4. Compressing the particles until they form a solid compact mass that surrounds the active end of the internal reference.
5. Introducing a metered quantity of electrolyte into the packed particle bed. This may be accomplished by using a micro pipette to place a tiny droplet of electrolyte on the upper surface of the packed particle bed. No special liquid handling steps are required because the capillary forces within the bed tend to draw the droplet into the bed and to distribute it uniformly throughout its fabric.
6. Sealing the electrolyte impregnated particle bed within the electrode body. This may be accomplished by, for example, covering the particle bed with a plug of a suitable epoxy cement such as 20 of FIG. 1.

Once the electrode seal has been formed, the electrode may be prepared for actual use in the same manner as any conventional liquid filled pH electrode.

Referring to FIG. 2, there is shown an alternative embodiment of the invention which is generally similar to that of FIG. 1, like functioning parts being similarly numbered. The principal difference between the embodiment of FIG. 2 and that of FIG. 1 is that, in the embodiment of FIG. 2, the seal 20' of the electrode is formed by heating the upper portion of the glass support member 12 until it softens and flows over conductor 15. The advantage of seal 20' is that it eliminates the need to use a separate sealing material. As a result, electrodes of the type shown in FIG. 2 may be inexpensively constructed from ordinary glass tubing.

Because an electrode of the type shown in FIG. 2 will ordinarily be relatively small, certain precautions should be taken in order to prevent the electrode from being damaged during the formation of seal 20'. This is because any appreciable contact between the liquid electrolyte and the molten glass of seal 20' can cause the electrode body to develop cracks. In order to prevent such cracks, it is advisable to modify the above described fabrication procedure by including the step of immobilizing the electrolyte during the formation of seal 20'. This may be accomplished, for example, by freezing the electrolyte by dipping the electrode body in liquid nitrogen prior to heating it to form molten seal 20'. This freezing assures that, by the time that the electrolyte thaws and comes into contact with seal 20', the glass of the seal will be sufficiently cooled to prevent the cracks from forming.

While the present invention has been described with reference to certain specific embodiments, it will be understood that these embodiments are for illustrative purposes only, and that the true scope of the present invention should be determined only with reference to the following claims.

What is claimed is:

1. A pH electrode which is capable of retaining its pH sensitivity in spite of repeated exposures to sterilizing temperatures, comprising:
    (a) an electrode body having a pH sensing member and a support member,
    (b) a bed of electrochemically inert particles packed within the electrode body adjacent to the sensing member,
    (c) an internal reference at least part of which is embedded in said bed,
    (d) a quantity of an electrolyte retained within said bed, the quantity of said electrolyte being large enough to establish electrical continuity between the sensing member and the internal reference, but small enough to prevent destructive pressures from arising within said body when the electrode is exposed to sterilizing temperatures, and
    (e) means for sealing the internal reference to the support member.

2. The electrode of claim 1 in which said particles are composed primarily of silica.

3. The electrode of claim 1 in which said particles are composed primarily of hydrated silica.

4. The electrode of claim 1 in which said particles are composed of glass.

5. The electrode of claim 1 in which the thermal expansion and contraction of the bed is adapted to track that of the electrode body.

6. The electrode of claim 1 in which said particles have a maximum size corresponding to approximately 100 mesh.

7. The electrode of claim 6 in which the quantity of electrolyte is approximately 20 to 100 microliters per cubic centimeter of the bed.

8. The electrode of claim 1 in which the tendency of the particles to adhere to the sensing member is similar to the tendency of the particles to adhere to one another.

9. The electrode of claim 1 in which said particles are small enough to produce capillary forces that are sufficient to distribute the electrolyte approximately uniformly throughout the bed.

10. The electrode of claim 1 in which the support member comprises a length of glass tubing, and in which the sealing means comprises a heat sealed portion of said tubing.

11. The electrode of claim 1 in which the support member comprises a length of glass tubing, and in which the sealing means comprises an electrochemically inert plug located at one end of the support member.

12. The electrode of claim 1 in which the bed is compressed into a substantially solid mass prior to the introduction of the electrolyte.

13. A pH electrode which is capable of retaining its pH sensitivity in spite of repeated exposures to sterilizing temperatures, comprising (a) a glass pH sensing member, (b) an electrically nonconducting support member for supporting and forming a liquid-tight seal with the sensing member, (c) said sensing and support members together defining an electrolyte retaining space, (d) a fluid retaining matrix comprising particles of an electrochemically inert material packed within said space, (e) a conductor having one end embedded in said matrix, (f) means penetrated by the conductor for fluidically sealing said matrix within said space, and (g) a quantity of an electrolyte fluid within said matrix, the quantity of said electrolyte being sufficient to establish fluidic continuity between the sensing member and the conductor, but not sufficient to produce destructive pressures within said space when the electrode is exposed to sterilizing temperatures.

14. The electrode of claim 13 in which said particles are composed primarily of silica.

15. The electrode of claim 13 in which the particles are composed primarily of hydrated silica.

16. The electrode of claim 13 in which said particles are composed of glass.

17. The electrode of claim 13 in which the particles have a maximum size corresponding to approximately 100 mesh.

18. The electrode of claim 17 in which the quantity of electrolyte is approximately 20 to 100 microliters per cubic centimeter of said space.

19. The electrode of claim 13 in which the tendency of the particles to adhere to the sensing member is similar to the tendency of the particles to adhere to one another.

20. The electrode of claim 13 in which the particles are small enough to produce capillary forces which are sufficient to distribute the electrolyte approximately uniformly throughout said space.

21. The electrode of claim 13 in which the support member comprises a glass tube, and in which the sealing means comprises a heat sealed portion of said tube.

22. The electrode of claim 13 in which the support member comprises a glass tube, and in which the sealing means comprises an electrochemically inert plug located at one end of said tube.

23. The electrode of claim 13 in which the bed is compressed into a substantially solid mass prior to the introduction of the electrolyte.

24. A method for fabricating a pH electrode which is capable of retaining its pH sensitivity in spite of repeated exposures to sterilizing temperatures, said method comprising the steps of:

(a) forming a pH electrode body having a pH sensing member and a support member, (b) filling at least the portion of the body which is adjacent to the sensing member with electrochemically inert particles, (c) inserting an electrical conductor into the particles, (d) compressing the particles into a solid bed, (e) introducing into the bed a quantity of electrolyte which is large enough to establish electrical continuity between the sensing member and the conductor, but which is small enough to prevent a pressure-initiated fracture of said body, and (f) forming a fluid tight seal between the conductor and the support member.

25. The method of claim 24 in which the particles are composed primarily of silica.

26. The method of claim 24 in which the particles are composed primarily of hydrated silica.

27. The method of claim 24 in which the particles are composed of glass.

28. The method of claim 24 in which the maximum size of the particles corresponds to approximately 100 mesh.

29. The method of claim 24 in which step (e) includes the introduction of from 20 to 100 microliters of electrolyte per cubic centimeter of the bed.

* * * * *